United States Patent [19]
Marlin

[11] Patent Number: 5,439,380
[45] Date of Patent: Aug. 8, 1995

[54] METHOD OF FORMING AN ABUTMENT POST

[76] Inventor: Gerald M. Marlin, 4400 Jenifer St., NW., Washington, D.C. 20015

[21] Appl. No.: 206,679

[22] Filed: Mar. 7, 1994

Related U.S. Application Data

[63] Continuation of Ser. No. 921,729, Jul. 30, 1992, Pat. No. 5,350,302, which is a continuation-in-part of Ser. No. 729,170, Jul. 12, 1991, Pat. No. 5,238,405, which is a continuation-in-part of Ser. No. 548,250, Jul. 5, 1990, Pat. No. 5,135,395.

[51] Int. Cl.⁶ .................... A61C 13/12; A61C 13/225; A61C 8/00
[52] U.S. Cl. ..................................... 433/172; 433/173
[58] Field of Search .............. 433/172, 173, 174, 175, 433/176

[56] References Cited

U.S. PATENT DOCUMENTS

| | | | |
|---|---|---|---|
| 4,854,872 | 8/1989 | Detsch | 433/173 |
| 4,955,811 | 9/1990 | Lazzara et al. | 433/173 |
| 5,004,420 | 4/1991 | Soderberg | 433/172 |
| 5,030,095 | 7/1991 | Niznick | 433/173 |
| 5,052,929 | 10/1991 | Seal | 433/173 |
| 5,106,300 | 4/1992 | Voitik | 433/173 |
| 5,125,841 | 6/1992 | Carlsson et al. | 433/172 X |
| 5,213,502 | 5/1993 | Daftary | 433/172 |
| 5,234,339 | 8/1993 | Greigereit | 433/172 |
| 5,259,759 | 11/1993 | Jorneus et al. | 433/173 |

*Primary Examiner*—NIcholas D. Lucchesi
*Attorney, Agent, or Firm*—William E. Mouzavires

[57] ABSTRACT

Abutment posts, gingival collars, and universal adaptors along with their fixation screws that are used for insertion into dental implants are revealed. The adaptor is universal in that it matches to many different shaped, sized, and styled implants, and standardizes their restoration with uniform gingival collars and abutment posts. A gingival collar of varying sizes, which extends from the top of the flange of the adaptor to the height of the gingival tissue, is used to bring the restoration of the implant into the oral cavity. A post becomes connected to the gingival collar to create a restoration for the placement of a crown or coping over the implant. The top of the adaptor has a projection which is indexed and the top of the gingival collar is also indexed. This indexing allows specific angle correction in the horizontal plane by the counter rotation of the gingival collar and the post head. The post head, itself, comes in a variety of angles and shapes to make vertical angle correction to compensate for angled implant placement. The combination of horizontal correction from the counter rotations of the gingival collar and the post head, along with the vertical angle correction of the post, allows for overall precise angle correction of implant placement.

19 Claims, 14 Drawing Sheets

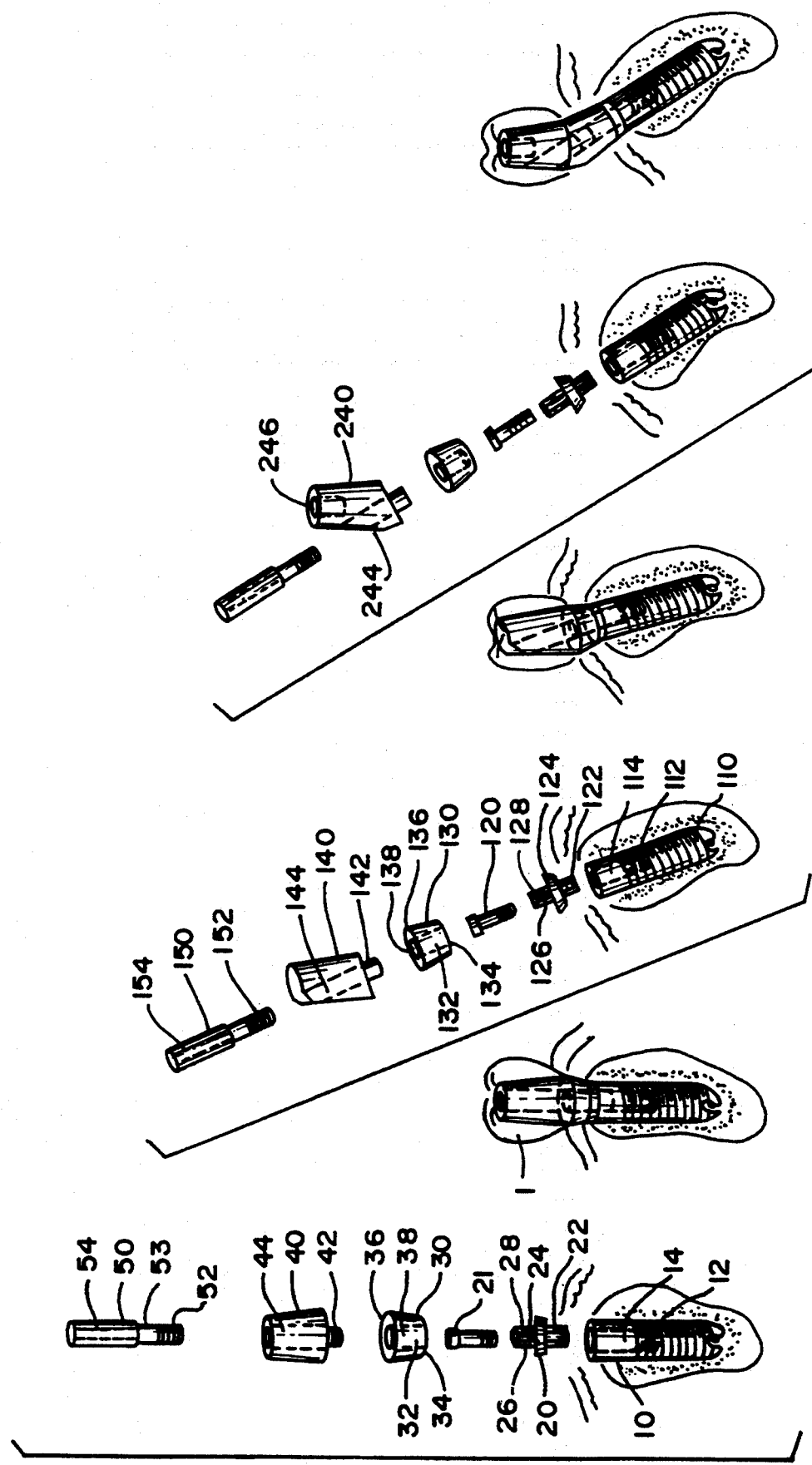

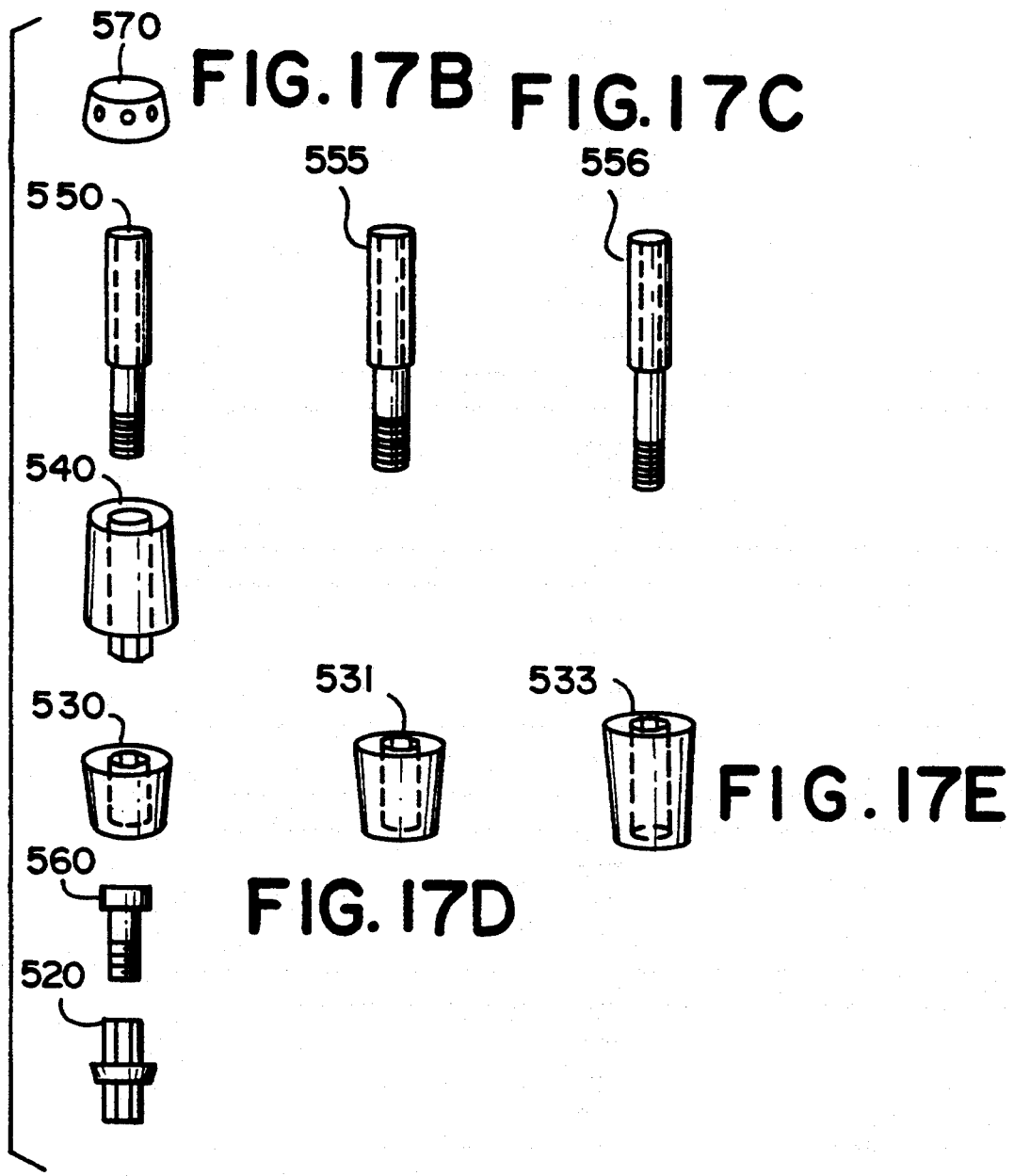

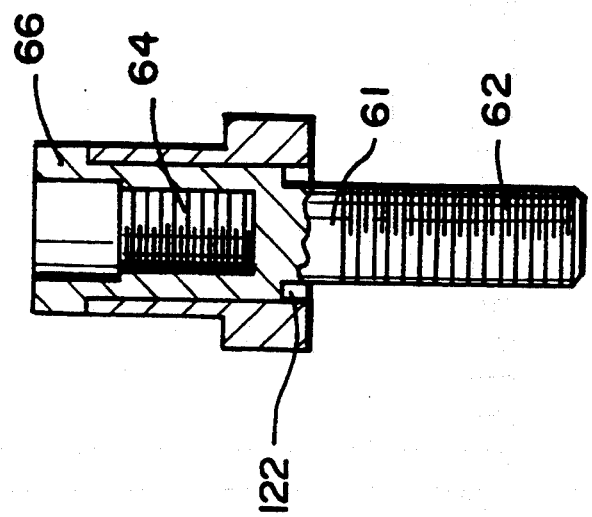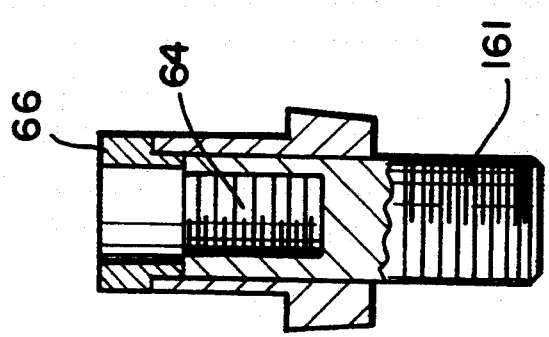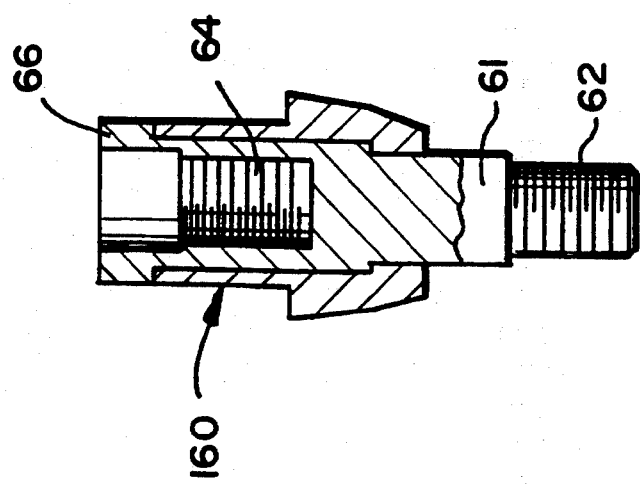

12,345,678,910

METHOD OF FORMING AN ABUTMENT POST

RELATED APPLICATION

This application is a continuation of my prior application, Ser. No. 07/921,729, filed Jul. 30, 1992 now U.S. Pat. No. 5,350,302 which is a continuation-in-part of prior application Ser. No. 07/729,170, filed Jul. 12, 1991, now U.S. Pat. No. 5,238,405 which in turn is a continuation-in-part of my prior application, Ser. No. 07/548,250, filed Jul. 5, 1990, now U.S. Pat. No. 5,135,395.

BACKGROUND OF THE INVENTION

This invention relates to the prosthodontic restoration of previously placed dental implants whereby a fixture, typically titanium, is surgically implanted in the edentulous area of the alveolar bone as a substitute for a missing natural tooth root.

The use of dental implants has proceeded rapidly since their commercial introduction to the dental community. Initial attention of implant restoration of the mouth was focused on the achieving of a sound integration of the titanium fixtures to the surrounding bone. Success was determined by the degree of this osseointegration. As the field grew in size and scope, a variety of sizes and configurations of implants became available to the dental practitioners. However, in the rush to provide biocompatible fixtures in the mouth, inadequate attention was paid to the needs of the restorative dentist in his role of providing restorations that are esthetic and functional over implants that were more frequently placed at an angle in that they would not be parallel to other implants or natural teeth. As a result, it was left to the restorative dentist to provide a great deal of ingenuity, while enduring time-consuming and expensive procedures in trying to make these implants serviceable and esthetic.

OBJECTS OF THE PRESENT INVENTION

One of the objects of the present invention is to provide a novel and improved collar and post system and a method of restoration for dental implants. Included herein are the methods and apparatus for restoring dental implants in a manner which overcomes the above noted problems.

A further object of the present invention is to provide such methods and apparatus which are applicable to many different styles, types, shapes, and sizes of implants including those presently used in restorative dentistry.

Another object of the present invention is to successfully address those problems of providing esthetic and functional restorations over previously placed angulated or malpositioned implant fixtures.

A further object of the present invention is to provide the ability to restore implants previously placed at angles up to sixty (60°) degrees off of the vertical.

A further object of the present invention is to provide a system that organizes the method by which previously placed implants are restored. The invention supplies methods and apparatus for simplifying the chairside (dentist) and laboratory (technician) techniques necessary to create high quality restorations, while compensating for angulations.

SUMMARY OF THE PREFERRED EMBODIMENT OF THE INVENTION

In the conventional restoration of implants, sequentially, at the initial surgical visit, the gum tissue is reflected to expose the underlying bone, and a titanium implant fixture is screwed or press fitted into the alveolar bone. Several months later, the gum tissue is opened to expose the implant to the oral environment. At that time and in accordance with the present invention, a universal adaptor is chosen and inserted to match the implant in place and secured with an anchor screw; a gingival collar of a height to correspond to the depth of the gum tissue is inserted; a transfer post is placed into the collar; and the post and collar are affixed to each other and to the universal adaptor with a fastener, preferrably a fixation screw. Impressions and bite registrations are taken and sent to a dental laboratory for fabrication of custom abutment heads and overlying crown restorations to ideal esthetic and functional parameters.

The laboratory technician pours a model around the impression, including a soft material around the replicas of the implants and their universal adaptors and gingival collars to represent the gingiva or gum tissue. Once he has the mounted models, the technician surveys the implants to the other teeth in the mouth and/or to other implants, so that all of the abutments are parallel to each other; so that they will provide crowns of natural contour and shape; and so that they will allow a good functional occlusion or bite. The correct gingival collar is chosen in a thermoplastic material, and inserted over the analog of the universal adaptor. Depending upon the degree of angulation of the implant, the technician will choose the correct thermoplastic abutment head to compensate for this angulation and allow "uprighting" of the implant. For small angulations, a precast gingival collar and abutment post may be chosen. For multiple implant abutments, once all of the abutment heads have been affixed to their analogs, the technician does the final "tooth preparation" according to accepted techniques on each post and bonds the thermoplastic collar and abutment head to each other. A precision abutment head to receive the crown or coping is now fabricated by casting the thermoplastic material into gold or other metal. This is done by encompassing it in a special stone with a sprue, and by then burning it out, leaving a space in the stone. The correct gold alloy or other metal is chosen, melted, and driven into the newly created hole. A precision cast abutment post has been created.

Various crowns are created to fit over the abutment posts, depending upon the various prosthetic considerations.

The restorative dentist removes the special healing cap or covering over the implants and their attached universal adaptors, and inserts the implant abutment, which will be in one piece, if it has been cast into gold or will be in one or two pieces if a precast titanium post is used (for smaller angulations). The post will fit over the previously placed universal adaptor that has been affixed to the implant by an anchoring screw which matches the threads of that particular implant and which receives the fixation screw. The combined abutment head and collar is affixed to the adaptor with a fixation screw, and the overlying crown is connected to the abutment head by either cementing it to it or by screwing one to the other.

DRAWINGS

Other objects of the present invention will become apparent from the following detailed description taken in conjunction with the accompanying drawings in which:

FIG. 1A is an axially exploded view of an implant in place, a type of universal adaptor and its fixation screw, a gingival collar, an abutment post, and a fixation screw in accordance with one embodiment of the present invention illustrating a straight-up or vertical implant;

FIG. 1B is a side elevational view of the assembled parts of FIG. 1A including a crown (final restoration);

FIG. 2A is a view generally similar to FIG. 1A except that it incorporates a modified post head to accomodate the angulation of the implant;

FIG. 2B is a side elevational view of the assembled parts of FIG. 2A;

FIG. 3A is a view generally similar to FIG. 2A except that it incorporates a modified post head to accomodate the further angulation of the implant;

FIG. 3B is a side elevational view of the assembled parts of FIG. 3A;

FIGS. 17A through 17E show an exploded view of a transfer system in accordance with the present invention;

FIG. 18A is another embodiment of the universal adaptor;

FIG. 18B is another embodiment of the universal adaptor;

FIG. 18C is another embodiment of the universal adaptor;

DETAILED DESCRIPTION

Figures 4A, 4B, 5A, 5B:
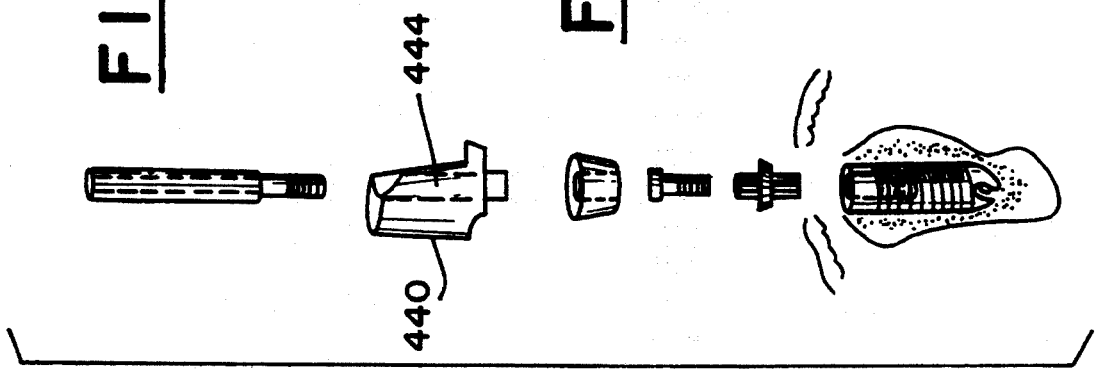
FIG. 4A is another embodiment of the invention at a more severe angulation. With precise fabrication by the laboratory technician, the implant angulation can be corrected by as much as 60°.
FIG. 4B is a side elevational view of the assembled parts of FIG. 4A.
FIG. 5A is an exploded view of another embodiment of the invention, showing restoration of an implant when it has been incorrectly placed in a vertical plane in space; the restoration compensates for the positioning of the previously placed implant.
FIG. 5B is a side elevational view of the assembled parts of FIG. 5A.

Referring to the drawings in detail, in FIG. 1A, the implant (10), itself is represented as it exists after placement in the bone. In this example, it has an internal bevel, a threaded portion (12) to receive a fixation screw (in this case the anchor screw thread), and a hexagon portion (14) which receives the hexagon stem of the universal adaptor. In another embodiment the hexagon receptor may be replaced by an internal bevel (FIG. 6A, 21), cylinder, etc. depending upon the internal configuration of the implant chosen by the manufacturer. The universal adaptor (20) has at one end an external hexagon stem or post (22) to fit inside the hexagon of the implant. This configuration may be replaced by other means of varying dimensions and of such a nature as to fit into several different types of manufactured implants with various dimensions and internal thread diameters. The post (22) fits into the receptor (14) in the head of the implant. It is connected to the implant by an anchor screw (21), which extends through the hexagon external post at the open end. In another, preferred embodiment to be discussed later, (FIG. 6A), the stem (66) of the anchor screw (60) extends beyond the octagon post at the free end. The anchor screw in that embodiment has an internal thread to receive the fixation screw. A small flange (24) tapers from the dimension of the individual implants (10) to a standardized size at its free end. An external post, octagon in shape (26), extends from the flange toward the free end. Any external posts (22 & 26) at the open and free ends have an internal opening to receive the anchoring screw (21). A gingival collar (30) of varying lengths to extend from the top of the flange to the height of the gingival tissue is used to extend the restoration of the implant into the oral cavity. It tapers from the open end (34) at the flange of the universal adaptor to a larger standardized size in order to more naturally represent the size and shape of a natural tooth root at the free end (36). It has an internal opening extending from the open end at the adaptor to the free end (36) of an octagon shape to receive the octagon posts of the "adaptor" (26) and the abutment post (40). In some instances, the abutment post has at one end an external octagon post (42) to be inserted into the octagon receptacle of the gingival collar. It has at its free end a socket to receive the fixation screw (50). The fixation screw, itself, has an internal hex hole which extends down the shank (54) to allow sizing of the screw by the laboratory technician without the need to cut a new slot for a screw driver. Once cut down, there is still a position for insertion of a hex tool to match. The shank (53) and the threads (52) match the corresponding parts of the octagon stud of the universal adaptor. FIG. 1B is a composite of the connection of the implant, anchor screw and universal adaptor, the gingival collar, and the abutment post and final crown (1).

The post is preferably made from a thermoplastic material to allow precision refining of the shape and comes in a variety of angulations (FIG. 2A, 140; FIG. 3A, 240; FIG. 4A, 340; FIG. 5A, 440) to compensate for an otherwise angulated implant that is not parallel to other teeth or implants. In FIG. 2A the abutment post is different as it corrects for an angulation of 15°, but all of the other parts are the same. The post has been reshaped to straighten-up the tooth preparation. During the set-up of the case, the laboratory technician will choose the post of the correct angulation to straighten up the tooth preparation to parallel it to other implants or teeth, and then will rotate it on the octagon (or the universal adaptor on the hexagon) to achieve the "optimum" position for the post. He then prepares the final tooth preparation. FIG. 2B is a composite drawing of the parts of FIG. 2A. FIG. 3A and 3B show the same relationships as FIG. 2A and 2B, except that the angulation of the post is 30° instead of 15°. The abutment post (240) has a hole for the fixation screw (244) and a separate hole (246) to receive a tube and screw appliance for fixation of the final crown by screwing it into place instead of cementing it, as the dentist chooses. In the preferred embodiment, the abutment head has a taper of no more than 10° to allow frictional retention of the crown. FIG. 4A and 4B show the same relationships as FIG. 3A and 3B. It also has a separate tube and screw receptacle (346). The dentist has the option to choose between cementing the crown or screwing it down.

FIG. 5A and 5B show a special post for correction of implant placement when it is at a reasonable angulation, but is placed too far mesially, distally, bucally, or lingually relative to other teeth in the arch. In addition, it corrects for placement of an implant whose restoration would impinge upon a solder joint of a bridge.

Figure 6A:
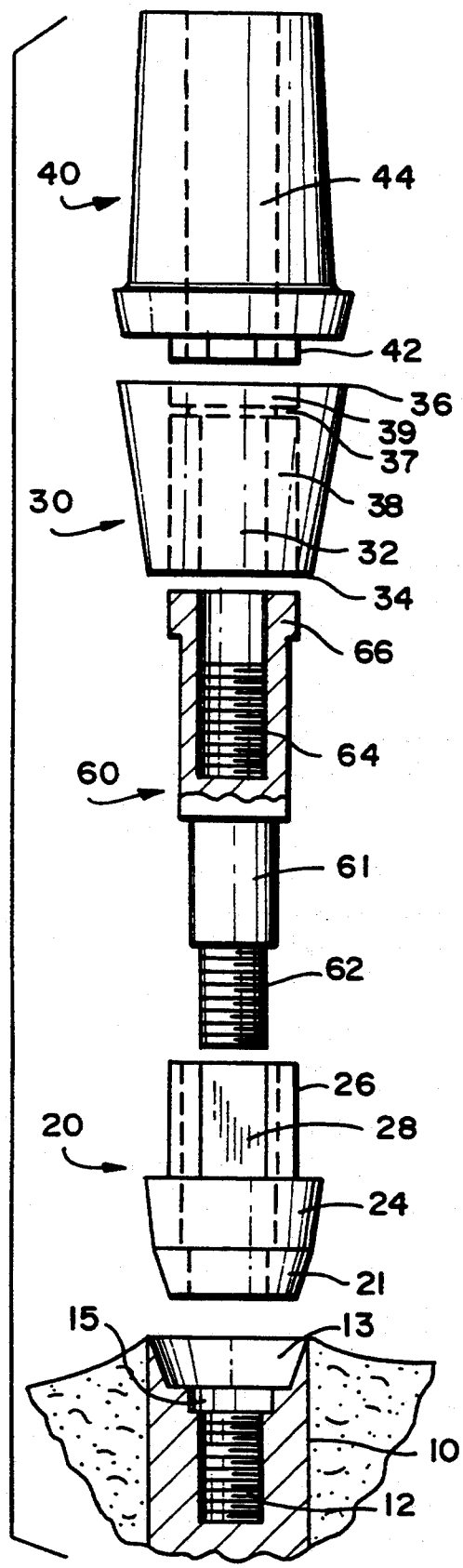
FIG. 6A is an enlarged, exploded, elevational view generally similar to FIG. 1A, but showing a preferred embodiment of the present invention.
Figure 6B:
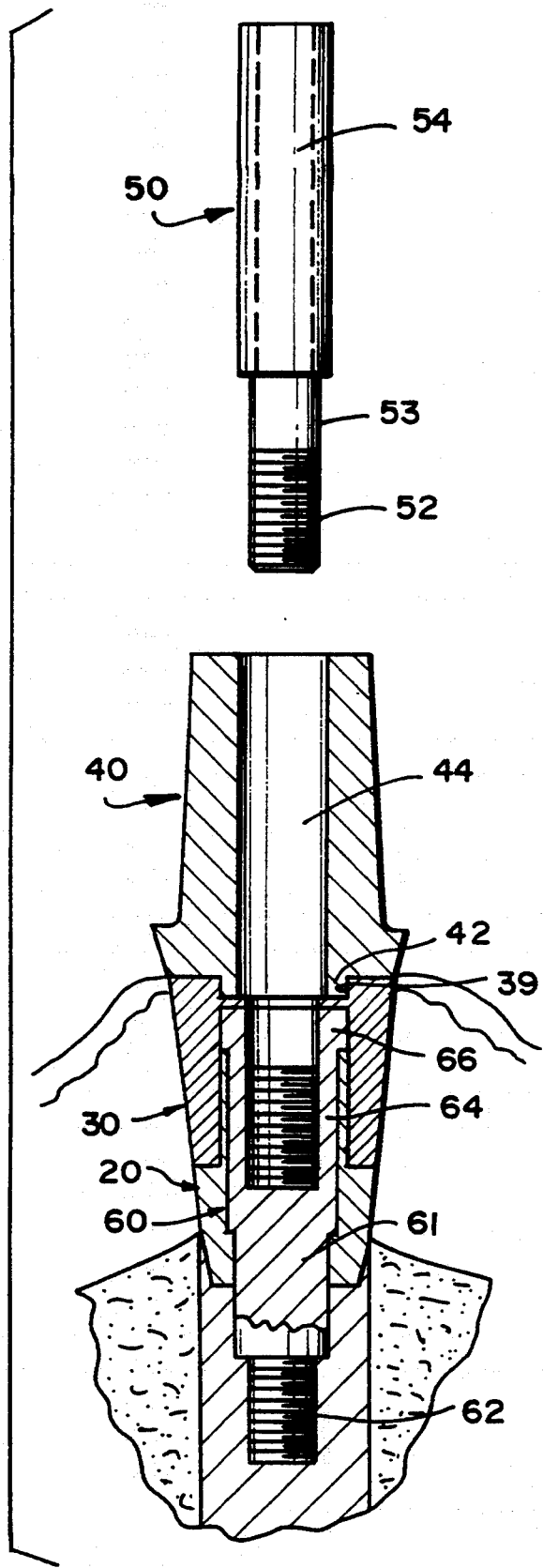
FIG. 6B is a side elevational view of the assembled parts of FIG. 6A.

FIG. 6A and 6B represent the preferred embodiment of the invention, except for the implant connection of the universal adaptor, which varies according to the implant to which it is connecting and except for the post head itself which varies according to angulation. In this example the implant (10), itself, is represented as it would exist after placement in the bone, and after osseointegration. It has an internal threaded portion (12) to receive some form of fixation screw for a prosthesis, in this case, the anchor screw thread (62). It usually has a cylindrical chamber (15) to receive the shank (61) of the anchor screw which is fabricated to match it. In this example, the implant has an internal bevel (13) which is matched to the tapered cylinder (21) below the flange (24) of the universal (octa-hex) adaptor. The Octa-HexTM adaptor, in this example, has the tapered cylinder (21) which fits inside the implant (13). There are many embodiments below the flange of the adaptor (20). It has a flange (24), which at its open end is the same size as the head of the implant and which tapers out to a greater dimension at its incisal or free end to a standard size for the system. It has a external stud of an octagon shape which allows a precise interdigitation along with the ability to rotate the parts above it in 45° increments. Because of its length, the octagon stud provides strength and resistance to fracture to the fixation screw. The anchor screw (60) threads into the implant (12) while its flange at the free end (66) tightens the universal adaptor on to the implant head. The gingival collar (30) comes in varying lengths to extend from the top of the flange (24) of the universal adaptor to the height of the gingival tissue and extends the restoration of the implant into the oral cavity. It tapers from the open end (34) at the flange to a larger standardized size in order to more naturally represent the size and shape of a natural tooth root at the free end (36). It has an internal opening (38) at the open end to receive the octagon stud of the universal adaptor, and has an internal cylindrical passage (32) to allow the fixation screw to pass through into the anchor screw. The gingival collar has an internal shoulder (37), which engages the post and collar combination (40 plus 30) into place, once their individual thermoplastic parts (30 and 40) are connected by the technician by bonding agent prior to casting into gold or other metal. They are now effectively one piece to be affixed to the anchor screw by the fixation screw as it engages the internal shoulder (37) while the threads combine. The gingival collar also has an octagon receptacle (39) to receive the octagon stud (42) of the post head. This octagon combination allows for rotation of the post head in the horizontal plane for a more precise placement of the post prior to connection to the gingival collar. The post head has an internal cylindrical passage (44) to receive the fixation screw (50). The fixation screw, itself, has an internal hex hole (54) which extends down the shank to allow sizing of the screw by the laboratory technician without the need to cut a new slot for a screw driver. Once cut down, there is still a position for insertion of a hex tool to match. The threads (52) engage the internal threads (64) of the anchor screw, while the head of the screw engages the internal flange (37) of the post/collar.

Although not shown in FIG. 6A, post head (40) may be secured to the collar (30) by a screw like screw (50) which will also serve to secure the collar to the adaptor.

There are many variations of the post head, some of which are presented here. The tooth abutments, themselves, are larger in size than most presently available in order to conform, more naturally, to the size of the roots and crowns of natural teeth. They sit on the gingival collar which is an inverted frustoconical shape and tapers-out up to the free end in the same manner as the natural root tapers-out from the apex of the root until it reaches the crown portion of the tooth. Another purpose of all of the post heads is to reangulate an otherwise malpositioned implant with respect to ideal placement in a dental arch; to provide a positive seat of the final crown with a circumferential chamfer or other means; and to prevent rotation of the final crown otherwise caused by a tapered cylinder as the tooth preparation which is sometimes presently used.

Figure 7:
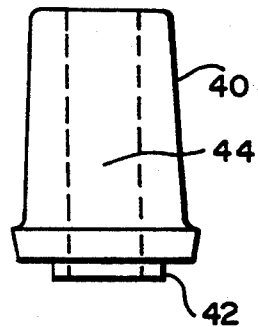
FIG. 7 is an enlarged elevational view of a nonangulated post included in the system of the invention.

FIG. 7 shows the basic embodiment of the post head, when the implant is perfectly placed in the mouth. Shown here is a chamfer preparation, which is one of many types of preparation available for these inventions. It has an external octagon stud (42) which interconnects with the octagon receptacle of the gingival collar. The fixation screw (50) passes through the channel (44) to the internal threads of the anchor screw. In another embodiment (not shown), the post head can be separately secured which would have an internal shoulder in the head and engage the anchor screw.

Figure 8:
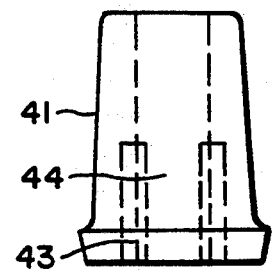
FIG. 8 is a view similar to FIG. 7, but showing another embodiment of a nonangulated post.

Another embodiment of the post head, the low profile head, is shown in FIG. 8. It has an internal octagon (44) to interdigitate with the octagon stud of the universal adaptor. The gingival collar is eliminated in order to have a short abutment height when the distance between the upper and lower jaws is reduced.

Figure 9A:
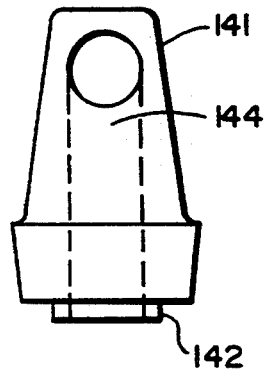
FIG. 9A is a view generally similar to FIG. 7 but showing an embodiment of an angulated post in accordance with the present invention.
Figure 9B:
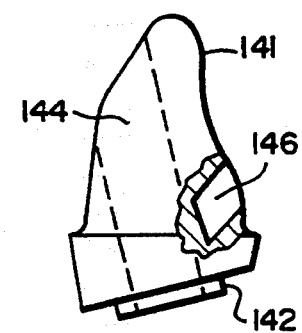
FIG. 9B is a side elevational view of FIG. 9A.

FIG. 9A and 9B show two views of an anterior abutment preparation (incisor or canine) of a 15° angulated abutment. It uses the same fixation screw, which exits from the channel (144) on the angulated surface. For those dentists that wish to have a screw down crown, a separate opening is provided on the lingual surface for esthetics (146) to place a tube and screw. The final crown can also be cemented into place, without the need for the tube and screw being used.

Figure 10A:
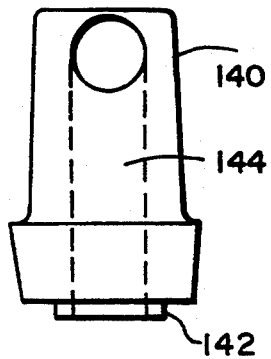
FIG. 10A is a view generally similar to FIG. 7 but showing an embodiment of an angulated post in accordance with the present invention.
Figure 10B:
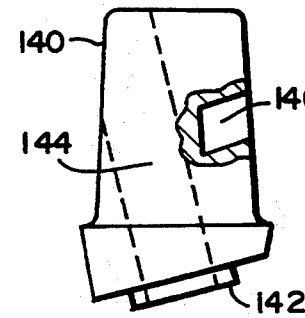
FIG. 10B is a side elevational view of FIG. 10A.

FIG. 10A and 10B is another embodiment of the 150 angulated abutment showing the restoration of the posterior (molar and premolar) implant. It also has a provision for a separate tube and screw (146) for fixation of the final crown, which can also be cemented.

Figure 11A:
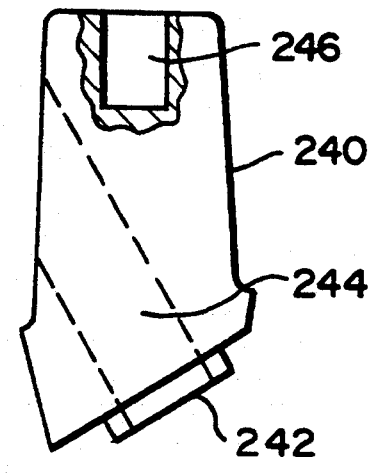
FIG. 11A is a view generally similar to FIG. 7 but showing an embodiment of an angulated post in accordance with the present invention.
Figure 11B:
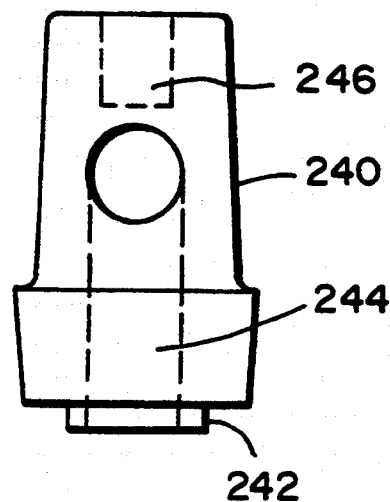
FIG. 11B is a side elevational view of FIG. 11A.

FIG. 11A and 11B are similar to FIG. 10A and 10B, but at a 30° angulation.

Figure 12A:
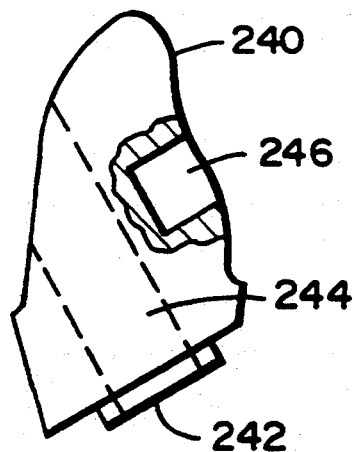
FIG. 12A is a view generally similar to FIG. 7 but showing an embodiment of an angulated post in accordance with the present invention.
Figure 12B:
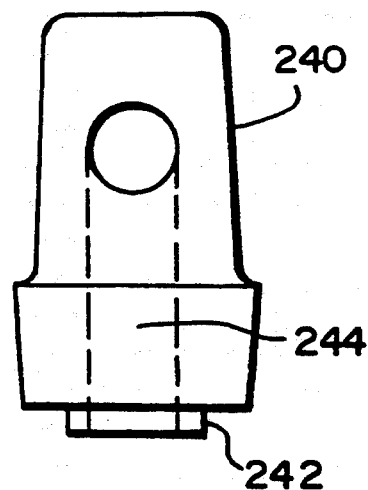
FIG. 12B is a side elevational view of FIG. 12A.

FIG. 12A and 12B are similar to FIG. 9A and 9B, but at a 30° angulation.

Figure 13A:
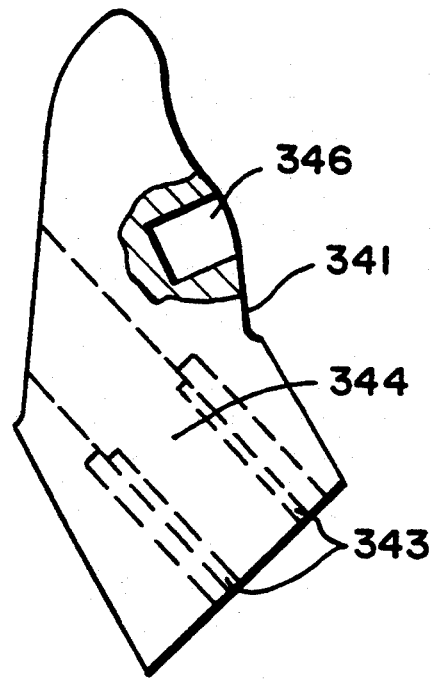
FIG. 13A is a view generally similar to FIG. 7 but showing an embodiment of an angulated post in accordance with the present invention.
Figure 13B:
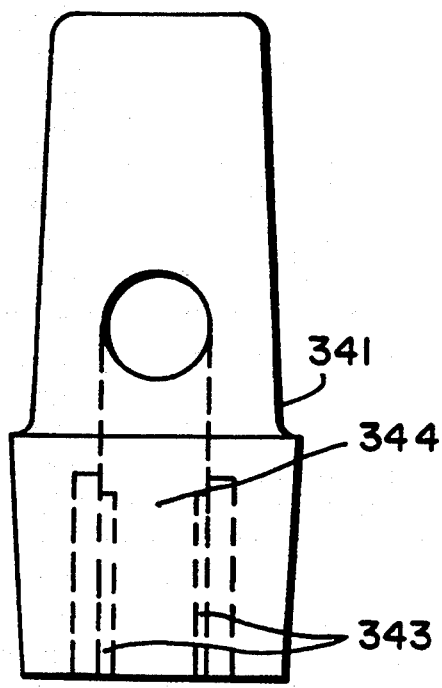
FIG. 13B is a side elevational view of FIG. 13A.

FIG. 13A and 13B are similar to FIG. 9A and 9B, but at a 45° angulation.

Figure 14A:
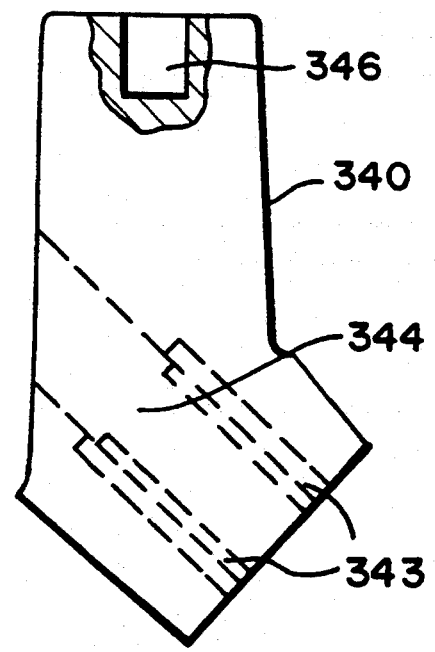
FIG. 14A is a view generally similar to FIG. 7 but showing an embodiment of an angulated post in accordance with the present invention.
Figure 14B:
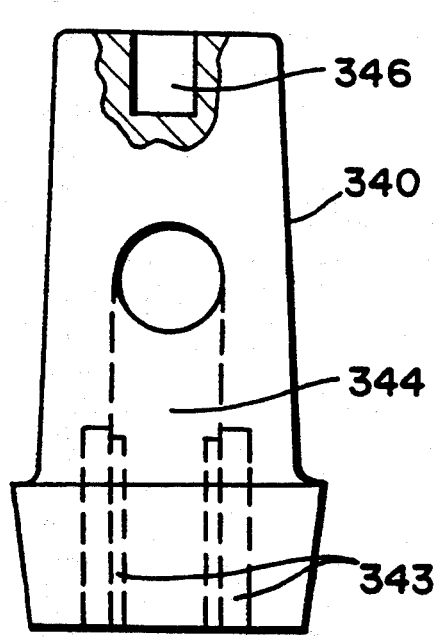
FIG. 14B is a side elevational view of FIG. 14A.

FIG. 14A and 14B are similar to FIG. 10A and 10B, but at a 45° angulation.

This invention is not limited to the angulations outlined above for these post heads, but, rather, the posts can be fabricated in any number of angulations to compensate from 0° to 45° (to 60° with preparation of the post by the laboratory technician).

Figure 15A:
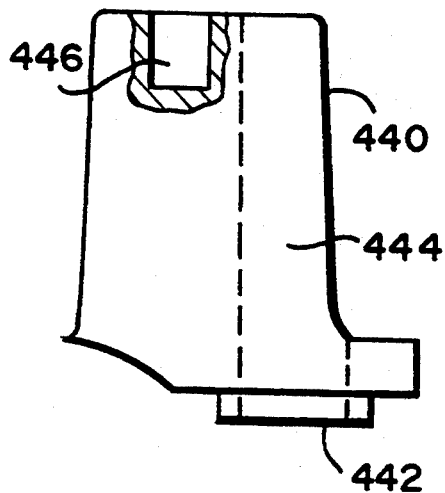
FIG. 15A is a view generally similar to FIG. 7 but showing an embodiment of an offset post in accordance with the present invention.
Figure 15B:
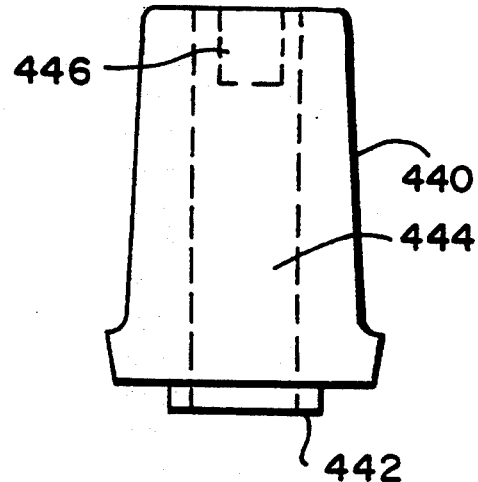
FIG. 15B is a side elevational view of FIG. 15A.

FIG. 15A and FIG. 15B is one embodiment of the vertical offset post, which changes the restoration of an implant in the vertical dimension in a specified measurement. The post head has a special design to allow the relative shifting of the position of the final crown, and has the availability of a opening for a tube an screw as described above.

Figure 16:
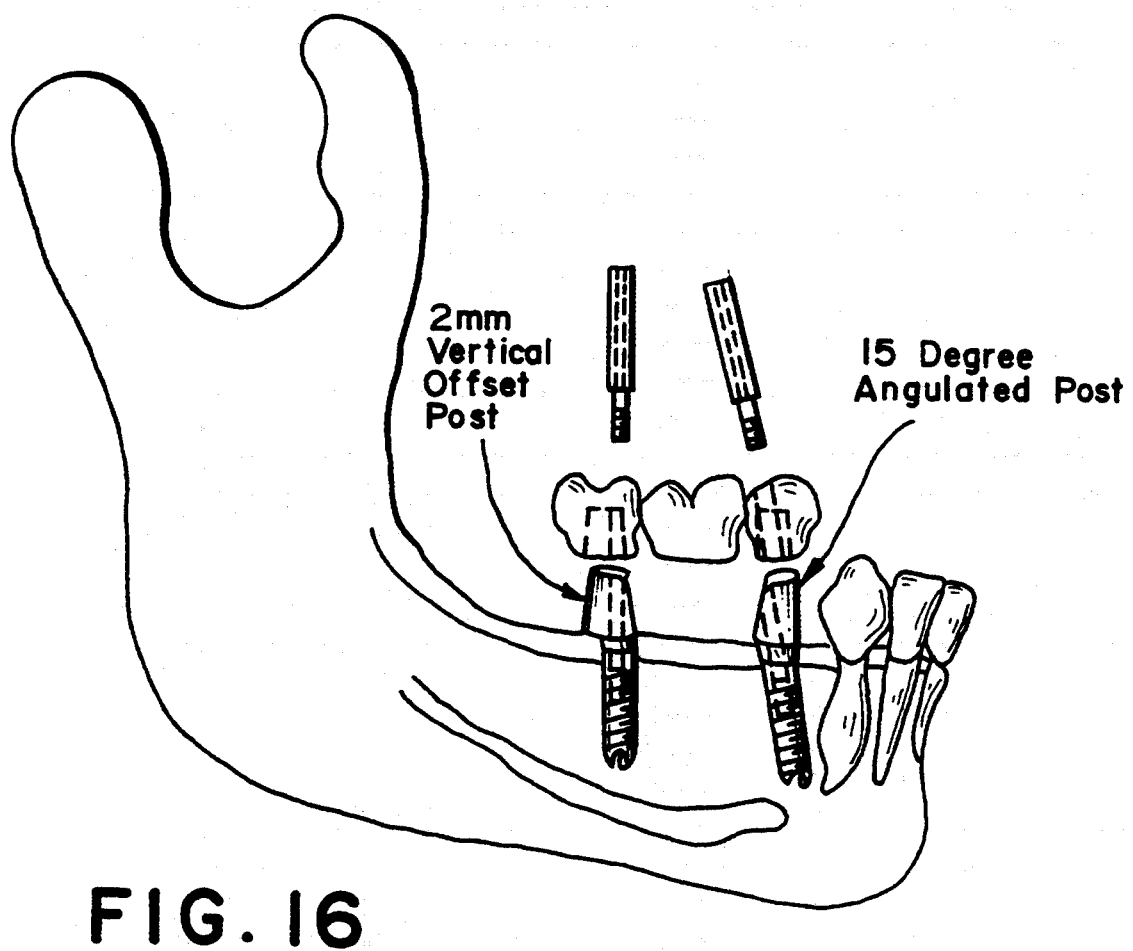
FIG. 16 is a side elevational view showing the system of the present invention assembled in the mouth ready for bridge insertion, after compensating for implant angulation and position.

FIG. 16 is a composite drawing of and angulated and misplaced implant having their relative positions corrected by corrective post heads of the Octa-HexTM system: the 15° post head and the vertical offset post head.

FIG. 17A,B,C,D,E shows the Octa-HexTM Transfer System parts. After the implants are exposed (4–6 months after insertion), the titanium universal adaptor (520) is inserted and affixed by anchor screw (560). The brass gingival collar (530) and transfer post head (540) are connected to the adaptor (520), and an acrylic transfer cap (570) is placed over the top to cover the hex opening at the top of the screw and to provide a positive seat in the impression. After the impression is taken, the brass analogs are disconnected and removed from the mouth, but the acrylic cap (520) remains in the impression.

FIG. 17A shows the brass or other metal analog of the universal adaptor (520) which is connected to a brass or other metal analog of the implant being restored (not shown) via the titanium or other metal anchor screw (560). The gingival collar (530) is connected along with the transfer post head (540) via a titanium or other metal fixation screw (550). The completely assembled parts are inserted into the impression, and will snap into the acrylic cap (570) that was retained in the impression when it was removed from the patient's mouth. A Coe-SoftTM or equivalent soft material is flowed around the brass analogs, and a dental stone is poured over that. A complete replica of the implants and the gum tissue around them is now ready for the technician to choose the correct posts; custom prepare them, if necessary,; cast them; and fabricate the final crowns.

This invention is not limited to a two piece collar and post system, which, in another embodiment (not shown), can be together combined into a one piece unit.

FIG. 17B and C show two different length screws (555, 556) to match, increasingly long gingival collars.

FIG. 17D and E show two different sized gingival collars (531, 533). There can be many sizes of gingival collars and fixation screws.

FIG. 18A is another embodiment of a universal adaptor (160) connected with an anchor screw, having a shank (61) and about to be placed into an implant. The anchor screw has threads (62) that are of such a nature as to match the thread characteristics of the designated implant as well as a shaft (61) to match. The anchor screw has internal threads (64) to receive the fixation screw and an external flange (66) to anchor the universal adaptor on to the implant while the screw is being threaded into the implant.

FIG. 18B is another embodiment similar to FIG. 18A except that the external thread of the anchor screw (161) matches another type of implant.

FIG. 18C is similar to FIG. 18A except that it has an internal hexagon (122) to match the designated implant's external hexagon.

It will thus be seen that the invention will allow the restorative dentist and the laboratory technician to provide the most accurate relationship esthetically (the look) and functionally (the bite) by compensating for the untoward angulations and positions which result from the surgical placement of the various titanium implants. At the same time, the invention will provide a uniformity in delivering this service, regardless of the type of implant which has been inserted into the edentulous alveolar bone by the surgeon. The same restorative dentist can treat his patients with several different surgeons, and, at the same time, provide each patient with equivalent restorative designs. The system provides precision, versatility, uniformity, and efficiency of delivery.

Figure 19A:
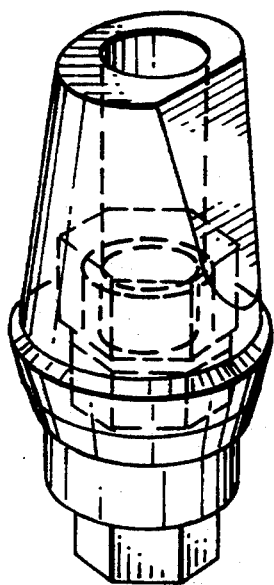
FIG. 19A is a perspective view of a post and collar system constituting a preferred embodiment of the present invention.

Referring now to FIGS. 19A and B, another system embodying the invention is shown as including an adaptor 420 having a hexagon shaped base 422 adapted to fit in a similarly shaped recess of an implant (not shown).

The adaptor 420 has shoulder 424 for receiving a collar 430. The latter has an internal octagon shaped passage at its lower end for receiving an octagon stud 426 projecting from the shoulder 424 of the adaptor 420. In addition, the collar 430 has an external surface 438 shaped as a hexagon adapted to the receive a similarly shaped hexagon surface 442 formed internally at the lower end of the post head 440. The post head of course fits on the shoulder 432 of the collar. The upper end of the collar has a cylindrical portion 439 for receiving the fixation screw.

Figure 20:
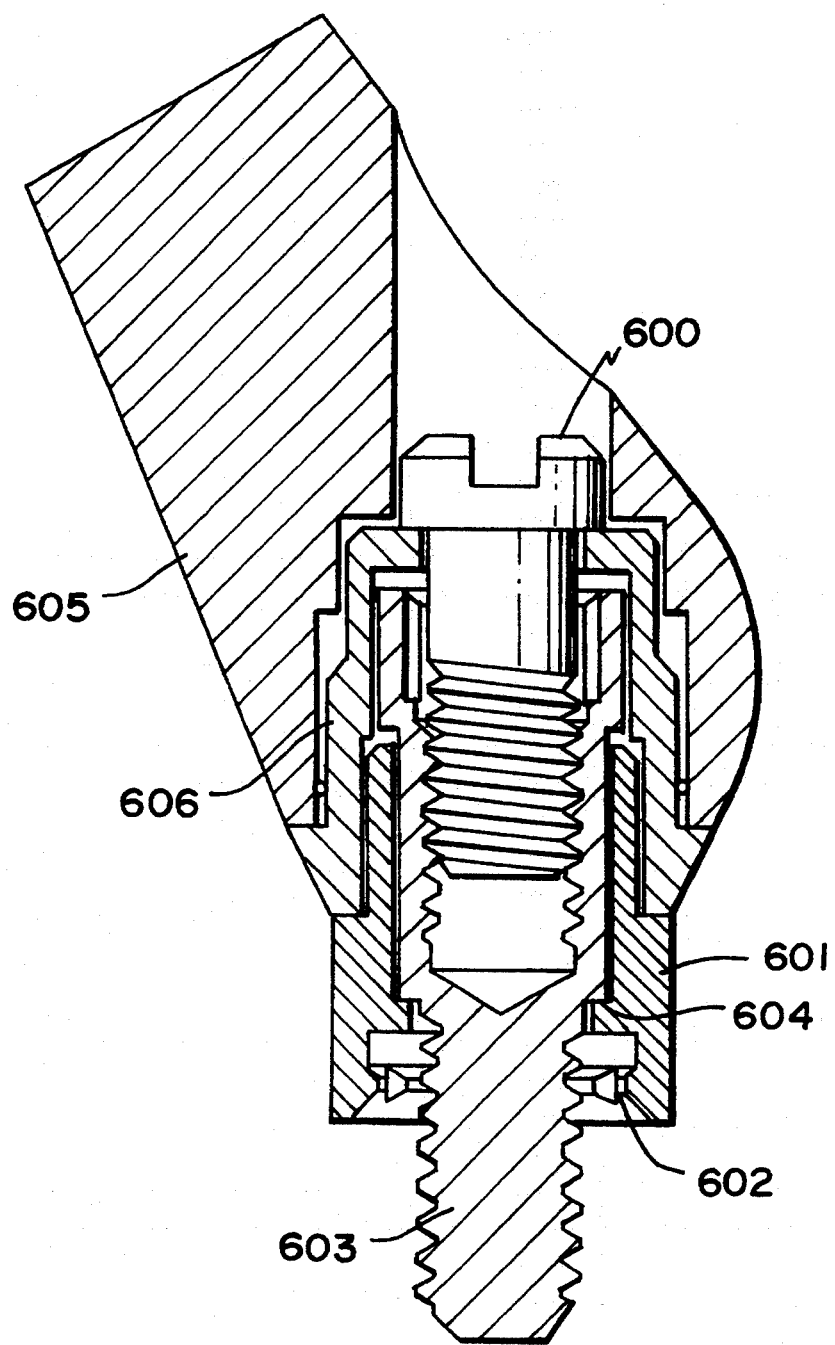
FIG. 20 is a cross-sectional view of another preferred embodiment of a post and collar system in accordance with the present invention and including an angulated post head and two screws for securing the assembly to an implant.

With this embodiment the collar 430 can be adjusted in one direction relative to the adaptor 420 and independently of the implant and regardless of the implant's indexing. Additionally, the post head 440 can be adjusted in a direction opposite to the adjustment direction of the collar 430 to provide minimum increments of adjustment of 15° degrees. In one method of assembly after effecting the horizontal and/or vertical angulation corrections, the plastic post head and collar are bonded together. In other embodiments they can be mechanically connected. After such connection the fixation screw anchors the combined post and collar to the adaptor via the anchor screw 600 as shown in the embodiment of FIG. 20. In this embodiment the adaptor 601 has an internal hexagon passage 602 to fit on a hexagon projection on the implant (not shown). The adaptor 601 is secured to the implant by screw 603 which has a shoulder that engages a shoulder 604 on the adaptor. Screw 600 is secured in screw 603 as shown in FIG. 20 to secure the combined post 605 and collar 606 to the adaptor 601.

Figure 19B:
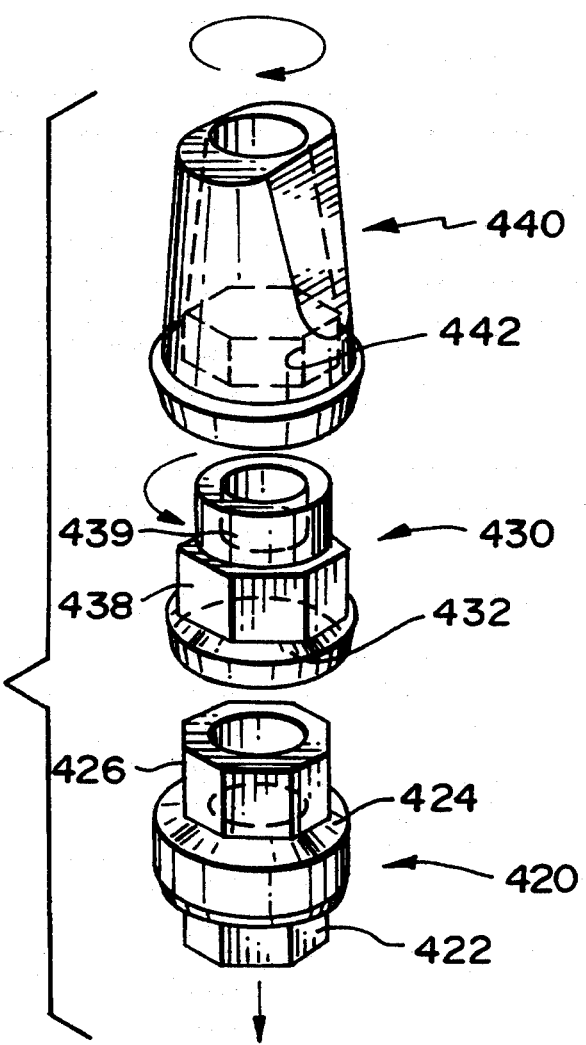
FIG. 19B is an exploded view of the system shown in FIG. 19A

Other different polyhedron combinations may be used instead of the specific octagon—hexagon combination described and shown in FIGS. 19A and 19B to give different minimum or maximum increment adjustments. Indeed other types of shapes may be employed. Also, it is possible to use a cylindrical surface instead of the hexagon surface 438 and a corresponding cylindrical female surface instead of the surface 442 in the post 440 (FIG. 19B). This would provide an infinite number of angulation correction—possibilities in the horizontal plane.

Figure 21:
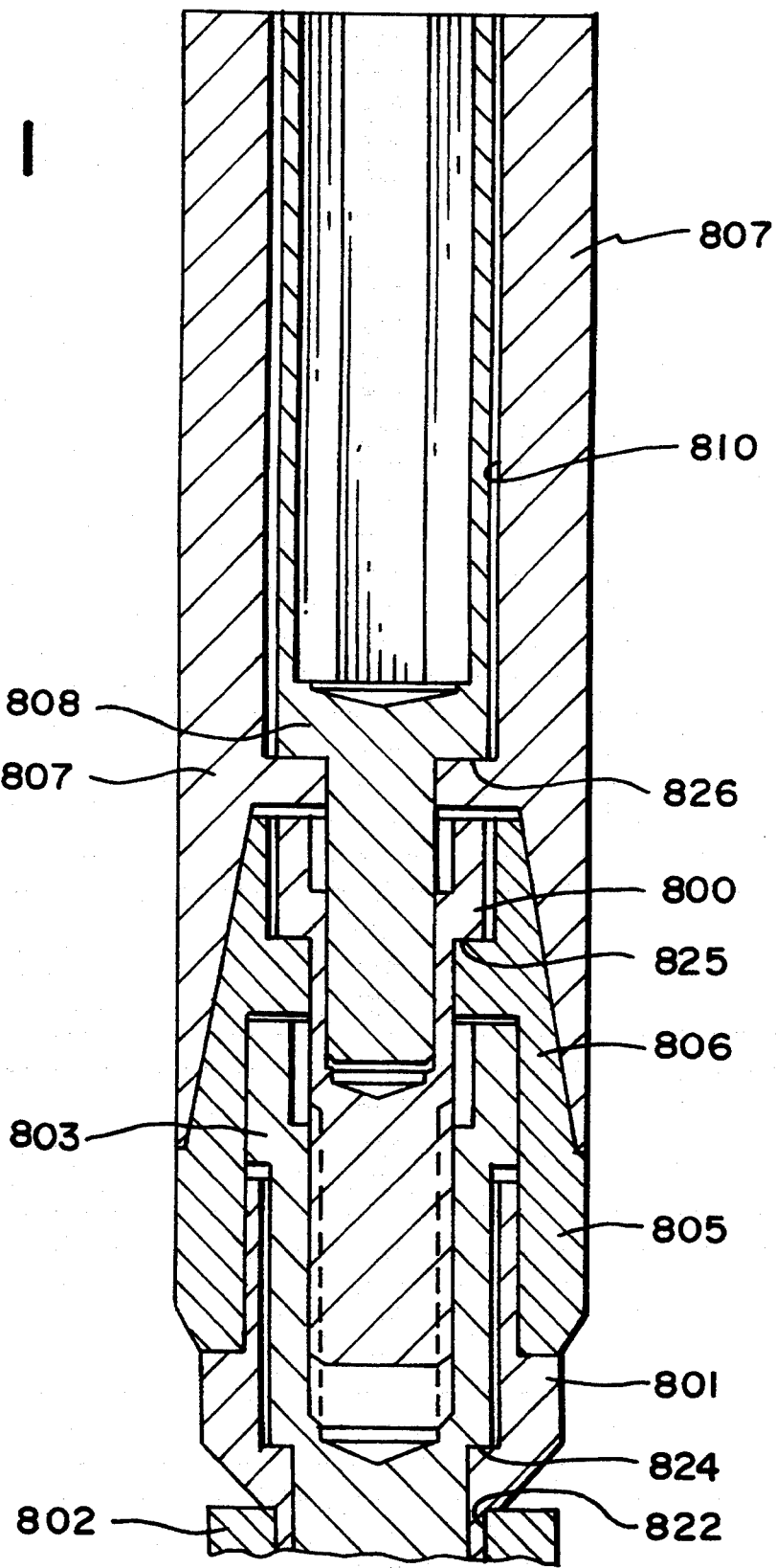
FIG. 21 is a cross-sectional view of another system embodying the present invention and including a combined post and collar and an additional connecting member and a third fixation screw.

Referring now to FIG. 21, another system embodying the invention is shown as including an adaptor 801 which has an external hexagonal connector stem 822 to fit on to an internal receptacle of an implant 802. The adaptor is affixed to the implant fixture by a fixation screw 803 which engages a shoulder 824 of the adaptor. An abutment post and collar combined into one piece 806 is affixed to the screw of first means 803 by a screw of second means 800 thereby connecting it to the adaptor. Screw 800 engages a shoulder 825 on the combined post and collar 806. A screw of third means 808 affixes a connecting member shown as a cylinder 807 in the specific embodiment or object of other shape to the abutment post 806. The combined post and collar may be made of other materials such as premade gold alloy, titanium, titanium alloy, ceramic or other suitable restorative material.

Figure 22:
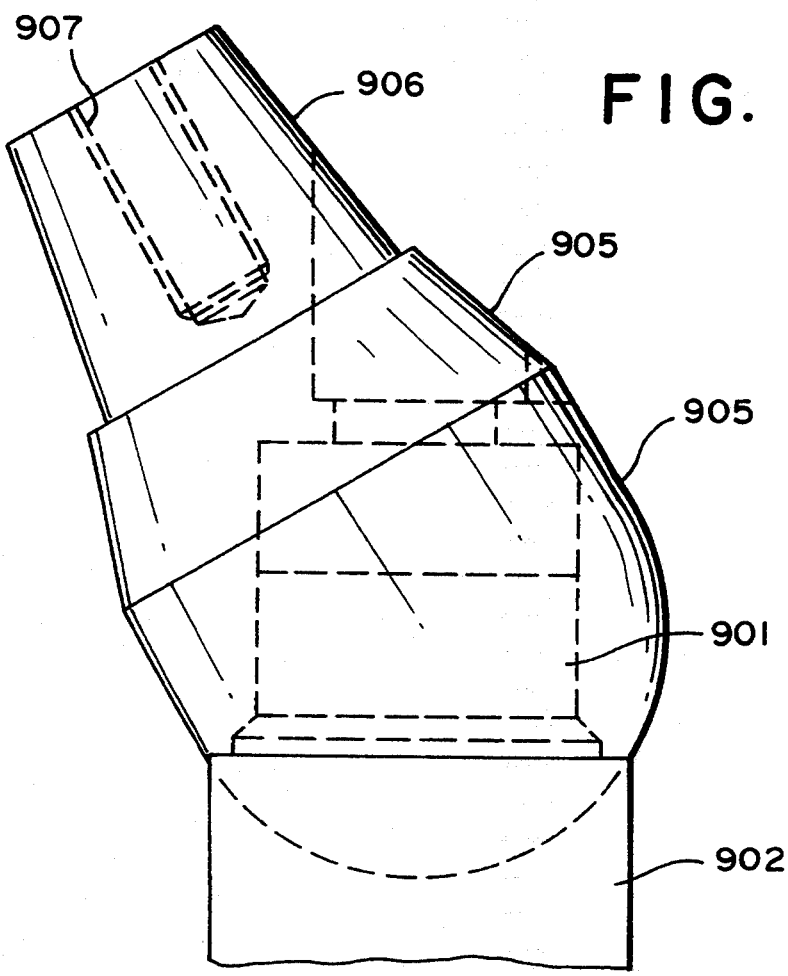
FIG. 22 is an elevational view of a system similar to that of FIG. 21 but with an angulated combined post and collar abutment.

Referring now to FIG. 22, another system embodying the invention is shown with an abutment piece 905 such as shown in FIG. 21 at an angle to the vertical plane. It has a tapered section at the top 906 to receive the cylinder 807 shown in FIG. 21 and an internal threaded portion 907 to receive a fixation screw 808 of third means shown in FIG. 21. The adaptor is shown at 901 and is secured by a first screw not shown to the implant 902. A second screw not shown secures the abutment 905 to the adaptor 901.

Figure 23:
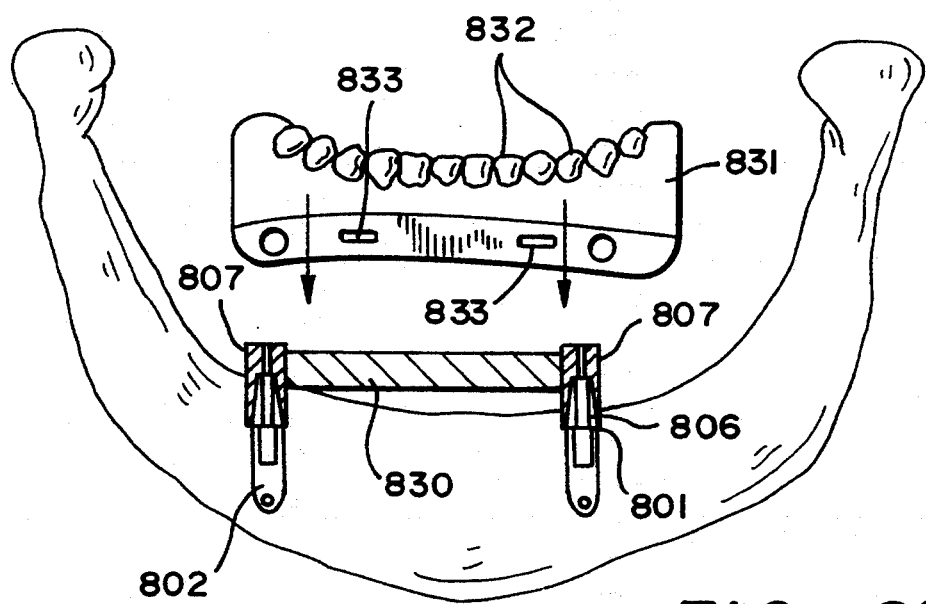
FIG. 23 is a cross-sectional view of an overdenture assembly secured to implants with a post and collar system of the present invention.

Referring now to FIG. 23, an overdenture assembly may be advantageously secured to implants 802 utilizing a post and collar system of the present invention. The assembly includes an overdenture 831 having teeth 832 for securement to an overdenture bar 830. Any suitable means such as clips 833 may be utilized to fix the overdenture 833 to the bar 830. The overdenture bar 830 in turn is secured to the implants 802 by means of the post and collar system of the present invention. In the specific embodiment shown, two systems are employed at opposite ends of the bar 830, each including a sleeve 807, a combined post and collar abutment 806 and an adaptor 801 such as described above and shown in FIG. 21. The system of the present invention may of course, be utilized to secure other types of restorative members to implants of various types.

Figure 24:
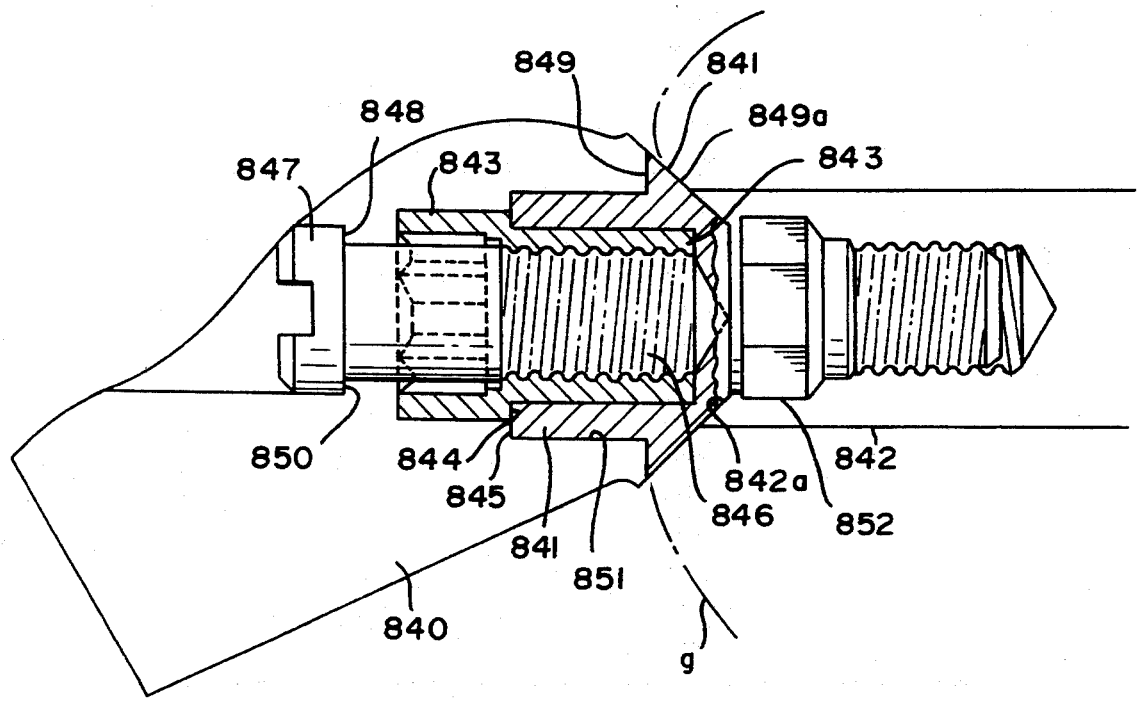
FIGS. 24 and 25 are other embodiments of the present invention.

Referring now to FIG. 24, another embodiment of the present invention is shown as including a post 840 dimensioned and shaped to receive a crown or coping (not shown). Post 840 is mounted on an adaptor 841 having an external annular shoulder 849 for receiving post 840 at the gum line g as shown. Below shoulder 849 the adaptor tapers downwardly and inwardly at 849a to a base portion 852 which fits into a similarly shaped passage portion in the implant. The mouth of the implant has an inverted frustoconical recess 842a for receiving the tapered surface 849a of the adaptor. Adaptor 841 is secured in implant 842 by a screw 843 having external threads engaged in complementary threads formed in the implant. Screw 843 has an external shoulder 844 engaged on a shoulder of the adaptor 841 shown as the end 845 of the adaptor, to secure the adaptor in the implant. Screw 843 has an internal slot or recess for receiving a tool or screw driver for fastening screw 843 into the implant 842. Screw 843 has internal threads 846 for receiving a second screw 847 which secures the post 840 on the adaptor 841. The securement is achieved by a shoulder 848 on the screw 847 which shoulder engages an internal shoulder 850 in the post 840. The post 840 has a through passage 851 for receiving the adaptor and screws 843 and 847.

Figure 25:
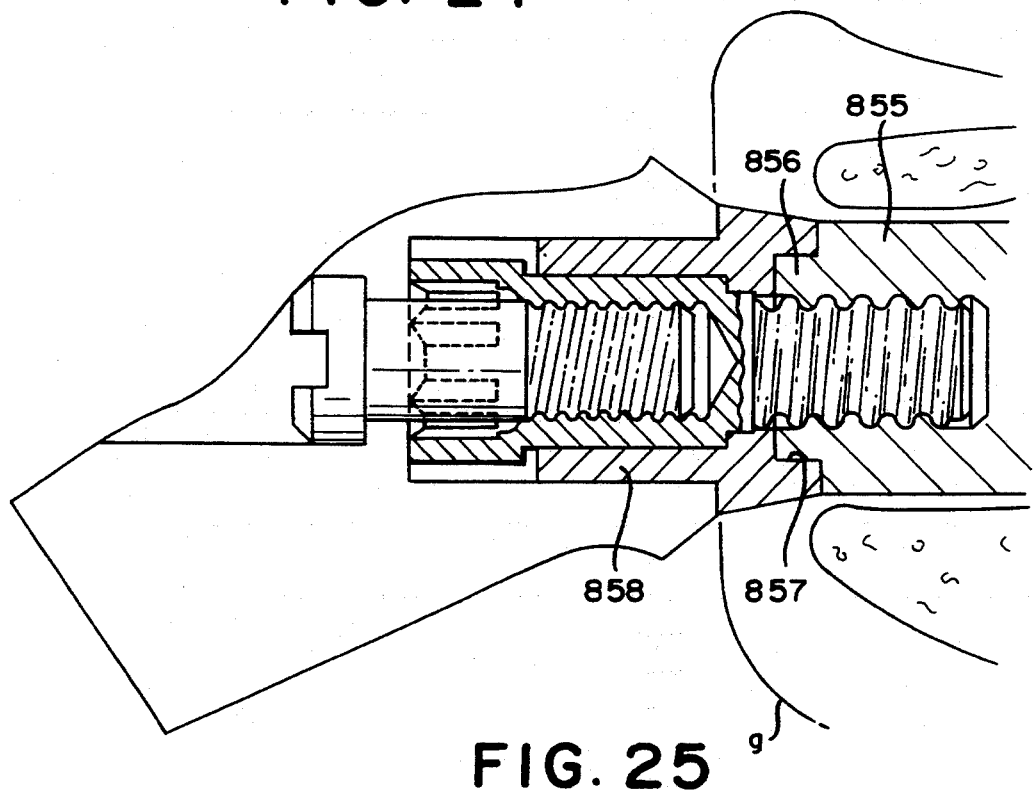

In the embodiment of FIG. 24 the external surface of the adaptor 841 has a polygonal shape, preferably an octagon, for receiving a similarly shaped internal surface at 851 of the post such that the post and adaptor may be angularly adjusted in increments. Of course other polygonal shapes or even cylindrical shapes may be employed instead in other embodiments. Angular adjustment of the adaptor relative to implant 842, in the embodiment of FIG. 24, is achieved by a hexagon-shaped outer surface at the lower end or base portion 852 thereof which surface fits into a similarly shaped surface in the passage of the implant. In other embodiments such as FIG. 25 wherein the implant 855 has a projecting hexagonal head 856, the lower end 857 of the adaptor 858 has an internal receptacle 857 having a hexagon shape for receiving the hexagon head 856 of the implant 855. The embodiments of FIGS. 24 and 25 may be used in situations where insufficient space exists above the implant in a patient's mount to receive a collar as well as an adaptor as in several of the embodiments described above.

Although several of the embodiments of the universal adaptor-anchor screw system have been shown and described above. There are as many embodiments as there are different types of implants to restore, especially external hexagons to match the more prevalent internal hexagons of the implants to be restored. Therefore, the scope of the present invention is not limited to the specific embodiments shown, but, rather, is defined in the appended claims.

I claim:

1. A method of making an abutment post which is used to receive a prosthesis in dental restorations, the method comprising the steps of applying a post part on a collar part and moving the parts relative to each other into a desired position, fixing the parts together, inserting the parts into a mold, and molding a one piece abutment post from the parts in the mold.

2. The method defined in claim 1 wherein the parts are made from thermoplastic material.

3. The method defined in claim 1 wherein the one piece abutment post is molded from gold material.

4. The method defined in claim 1 including the steps of making a model of a patient's teeth, and rotating the parts relative to each other while they are on the model.

5. The method defined in claim 4 including the step of mounting said collar and said post to an implant imbedded in a patient's jaw bone, and taking an impression of the patient's teeth including the collar and post attached to the implant, and forming the model from the impression.

6. The method defined in claim 5 including the step of using an adaptor to fit into the particular implant in the patient's mouth, and mounting the collar and post to the adaptor prior to taking the impression.

7. The method defined in claim 6 including the step of removing the collar and post from the patient's mouth after taking the impression while leaving the adaptor in the implant, and then applying a sealing cap over the adaptor in the patient's mounth.

8. The method defined in claim 5 including the step inserting the post and collar into the impression prior to forming the model.

9. The method defined in claim 1 wherein the parts are rotated relative to each other to position them at a desired angle.

10. A method for securing a dental crown to an implant in the mouth of a patient, comprising the steps of mounting a first abutment post to the implant, taking a bite impression from the abutment post, removing the first abutment post from the implant, forming a model of the abutment post from the impression, selecting a thermoplastic abutment post corresponding to the model and preparing the thermoplastic abutment post into a desired configuration corresponding to the desired crown, casting the prepared thermoplastic abutment post into a suitable abutment post, securing the suitable abutment post in the implant and attaching a crown to the suitable abutment post.

11. The method defined in claim 10 wherein the suitable abutment post is made of gold.

12. The method defined in claim 10 further including the steps of inserting an adaptor in the implant and a collar on the adaptor prior to mounting the first abutment post, mounting the first abutment post on the collar and leaving the adaptor in the implant when the first abutment post is removed together with the collar.

13. The method defined in claim 10 including the steps of selecting a thermoplastic collar and preparing the collar, connecting the thermoplastic collar and first abutment post together and casting them together into a single abutment post to be secured to the implant.

14. The method defined in claim 10 wherein an adaptor is secured in the implant and the abutment posts are mounted to the adaptor.

15. The method defined in claim 14 wherein the abutment posts are releasably secured relative to the implant by a screw extending in the adaptor.

16. The method defined in claim 14 wherein the adaptor is secured relative to the implant by a first screw member, and the abutment posts are secured relative to the adaptor by a second screw member.

17. The method defined in claim 10 wherein a cap is placed over the first abutment post, the bite impression is taken with the cap on the first abutment post and the cap is left in the impression while the first abutment post is removed from the impression.

18. The method defined in claim 10 wherein the first abutment post is chosen from a number of posts depending upon the degree of angulation, if any, of the implant.

19. The method defined in claim 1 wherein the one-piece abutment post is molded from ceramic material.

* * * * *